United States Patent [19]

Kremenchugsky et al.

[11] Patent Number: 5,339,223
[45] Date of Patent: Aug. 16, 1994

[54] SERVOCONTROL FOR FIBEROPTIC PHOTOTHERAPY PAD

[75] Inventors: Vladimir Kremenchugsky, Reisterstown; Anthony Buttitta, Ellicott City, both of Md.

[73] Assignee: Ohmeda Inc., Liberty Corner, N.J.

[21] Appl. No.: 36,612

[22] Filed: Mar. 24, 1993

[51] Int. Cl.$^5$ .............................................. F21V 8/00
[52] U.S. Cl. .................................. 362/32; 362/276; 362/802; 385/115; 385/901; 606/16
[58] Field of Search .............. 385/115, 117, 147, 901; 606/1, 2, 13, 16; 362/32, 276, 802

[56] References Cited

U.S. PATENT DOCUMENTS

| | | | |
|---|---|---|---|
| 3,125,013 | 3/1964 | Herrick, Jr. et al. | 362/32 |
| 3,430,057 | 2/1969 | Genahr | 385/115 |
| 3,754,988 | 8/1973 | Barnes | 385/147 |
| 4,234,907 | 11/1980 | Daniel | 362/32 |
| 4,366,529 | 12/1982 | Takahashi et al. | 362/32 |
| 4,415,952 | 11/1983 | Hattori et al. | 362/32 |
| 4,631,675 | 12/1986 | Jacobsen et al. | 362/32 |
| 4,763,984 | 8/1988 | Awai et al. | 385/31 |
| 4,907,132 | 3/1990 | Parker | 362/32 |

OTHER PUBLICATIONS

*The American Pediatric Society/Society of Pediatric Research,* May 1991, Bright Light is the Right Light: Multicenter Trial of a Novel Phototherapy Device.
*Clinics in Perinatology,* vol. 17, No. 2, Jun. 1990, Blue Light, Green Light, White Light, More Light; Treatment of Neonatal Jaundice—pp. 467-481.

*Primary Examiner*—James C. Yeung
*Assistant Examiner*—Alan B. Cariaso
*Attorney, Agent, or Firm*—Roger M. Rathbun; Larry R. Cassett

[57] ABSTRACT

A system for controlling the amount of light radiation directed upon an infant from a fiberoptic phototherapy pad by feedback from a light detector that itself is a fiberoptic pad. The fiberoptic detecting pad receives and detects the light density radiation over an area and is located intermediate the normal fiberoptic phototherapy pad and the infant and therefore is in the best position to detect accurately, the light impinging upon the infant. In some embodiments, the light detector pad is manufactured as part of the fiberoptic phototherapy pad itself as a unitary construction. Light readily travels through the light detector to the infant, yet the light detector senses the light intensity and density of the light passing therethrough.

28 Claims, 9 Drawing Sheets

SERVOCONTROL FOR FIBEROPTIC PHOTOTHERAPY PAD

BACKGROUND OF THE INVENTION

This invention relates to a system and method of controlling the output of a fiberoptic phototherapy pad, and, more particularly, to a system and method for sensing the light intensity of a fiberoptic phototherapy pad and for providing a servocontrol to deliver a prescribed amount of light therapy to an infant.

Hyperbilirubinemia is an affliction of newborn infants typified by an elevated level of a toxic molecule known as bilirubin in the infant's blood. Current medical therapy for such affliction is through the use of phototherapy where light radiation, generally within certain desired wavelengths, is directed upon the infant's skin. The most widely used means currently is through banks of lights that are placed over the infant and which direct the light in the desired path to impinge upon the infant. While effective, such lights are cumbersome in that they interfere with personnel attending to the infant and also generate undesirable heat surrounding those personnel. Additionally, since such lights are occasionally moved, adjusted, turned off for various reasons during attending the infant, it is difficult to accurately access the actual amount of phototherapy provided to the infant.

A more recent innovative commercial means of combatting hyperbilirubinemia is by means of a fiberoptic light pad or blanket that is made of optic fibers. One such commercial product is shown and described in Daniel, U.S. Pat. No. 4,234,907 and where the optical fibers are used as warp fibers in a commercial loom and woven with normal threads (weft threads) to produce a fabric having interwoven optical fibers and regular threads. As the optical warp fibers are woven with the weft fibers, the bending of the optic fibers emits the light in a desired pattern.

There are many advantages to the fiberoptic pad over the conventional light systems, one of them being that the pad itself contacts the infants skin and therefore the light actually reaching the infant is more accurately controlled since each infant may have the fiberoptic pad placed in the same relative position with respect to its skin. Thus, unlike lights that may be varied, moved etc, the dosage afforded to the infant can be accurately administered.

With the advent of accurate administration, therefore, it is now possible and desirable to precisely apply a known amount of light therapy to the infant. Additionally, as the science of light therapy advances, more insight is being gained with respect to the amount of light and the desirable wavelengths to be utilized. As to the wavelengths, an improvement to the accuracy of the wavelength of light incident on the infant is provided by the use of a monochromatic light source such as a laser as disclosed in copending U.S. Patent application entitled "Laser Phototherapy" and assigned to the present assignee.

Likewise, since precise wavelengths are thus possible and clinicians can thus study the effect of differing wavelengths on the reduction of bilirubin, it still remains that the dosage or light density cannot be accurately controlled. At present there is no means of accurately determining the dosage of light therapy and therefore no means of applying a known dosage to the infant.

As a part of the problem of controlling the dosage, even if a known intensity of light is established at a phototherapy pad, over time, the light source may diminish and therefore the light originally established becomes more and more reduced with time. With no means of detecting that reduction and taking some compensating steps, the attempt at delivering an accurate dosage, predetermined dosage is difficult.

That the dosage is important in reducing bilirubin; note the Abstract of a paper presented at The American Pediatric Society, Society of Pediatric Research at New Orleans, La. in May of 1991 entitled, "Bright Light is The Right Light: Multicenter Trial of a Novel Phototherapy Device" in which the efficacy of phototherapy was improved by increasing the intensity of the light radiation applied to the infant.

SUMMARY OF THE INVENTION

In accordance with the present invention, a system and method is utilized to detect and control the light intensity of light administered to an infant for phototherapy.

The system and method of the present invention utilizes a light detecting means to determine the intensity of light incident upon the infant and using that light intensity to signal a feedback system that feeds that information back to a servo control system. Obviously, such a light detecting means should be positioned as near to the light output as possible so as to gain an accurate signal of the light administered to the infant and yet should be as near as possible to the infant so that it accurately detects the incidence of light radiation actually reaching and providing therapy to the infant.

It is also desirable, of course, that the light detecting device not materially interfere with the light applied to the infant, since any such diminution of the light from the fiberoptic pad would have a deleterious effect on the light therapy or, alternatively, require additional power to the light source to overcome the diminution of light.

Accordingly, as a first requirement, the light detecting means used with the light controlling system should be located at the precise output of the phototherapy pad and also be as close to the infant as possible. As a preferred embodiment, the light detecting means may be a part of the make-up of the phototherapy pad itself and thus be woven directly into the pad. In any event, the detector means is closely associated with the output of light from the phototherapy pad and the infant.

As a second requirement, the light detecting means that can be used as part of a light controlling system cannot interfere, to any real extent, with the transmission of light from the phototherapy pad to the infant.

Finally, since the phototherapy pad itself administers light over an area, it is important not to just detect the intensity of light at a point since that point may not be indicative of the overall light being administered to the infant. Therefore, preferably, the light detecting means should be capable of detecting an average light density, that is, representative of the total optical power (or radiant flux) related to the overall pad area and expressed of terms of watts or Joules per second. However, since the area of the phototherapy pad and the patient skin area are not the same and vary from patient to patient, it is convenient for the clinician to know the average light density across the pad. Therefore, the light measurement system should be calibrated in units of light density, expressed in terms of watts per square unit.

As part of the control method and system of the present invention, the light feedback is used to control the actual light output from the phototherapy pad and thus the output may be controlled accurately and maintained at desired levels despite general degradation of the light source or other factors that might affect the light output.

Since the patient is in direct contact with the fiberoptic pad, there is some pressure applied to the flexible fiberoptic pad itself. This pressure can possible change the geometry of the various emitting layers, and, as a result, change the level of emittance or the distribution of light radiation from the phototherapy pad to the infant. Because light emission becomes a function of weight (size) of the patient, to achieve the best accuracy, light measurement should thus be provided when the phototherapy pad is applied to each patient.

These and other improvements and features of the present invention will become better understood from the detailed description of the preferred embodiment set forth below taken In conjunction with the accompanying drawings.

DETAILED DESCRIPTION OF PREFERRED EMBODIMENT

Figure 1:
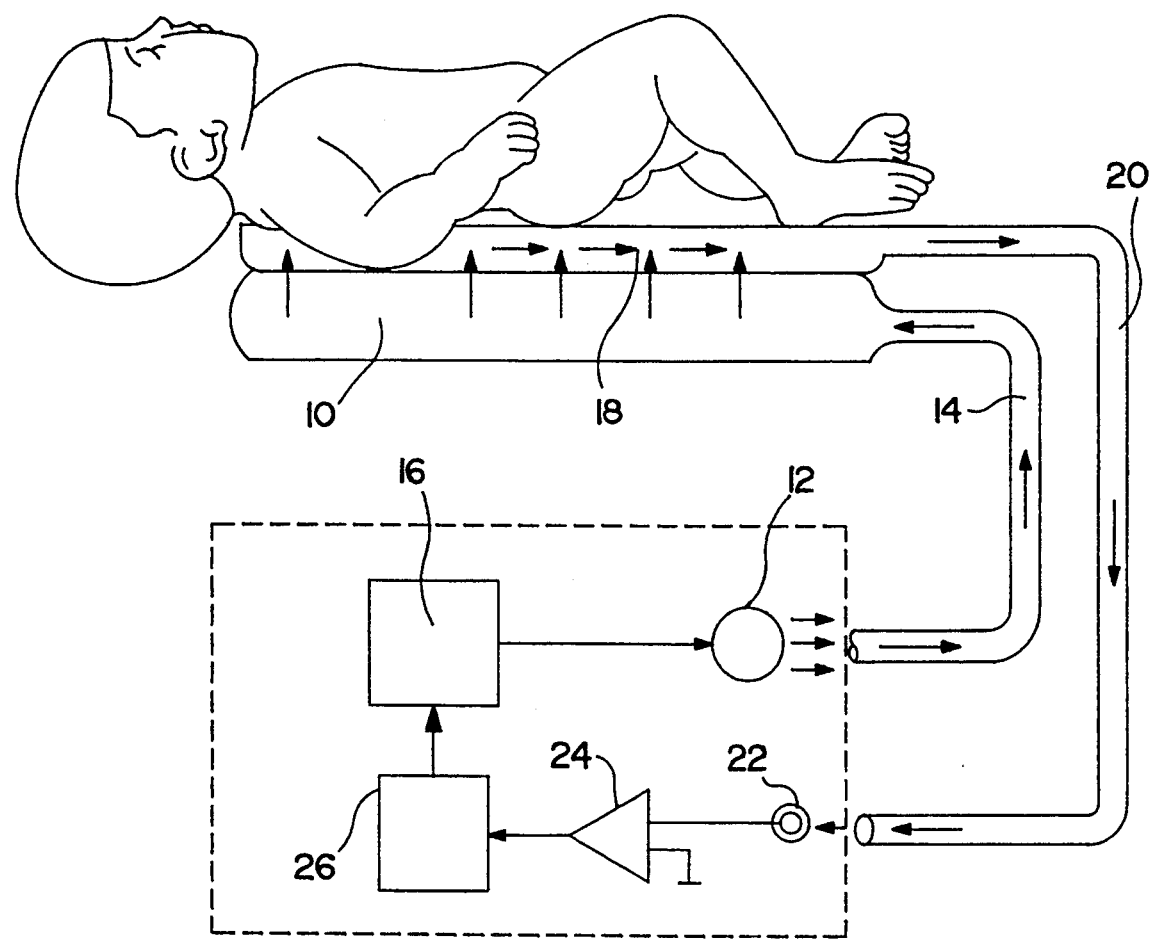
FIG. 1 is a schematic view of a fiberoptic phototherapy system having a feedback system constructed in accordance with the present invention.

Turning first to FIG. 1, there is shown a schematic view of a fiberoptic phototherapy control system constructed in accordance with the present invention and including a fiberoptic pad 10 adapted to be placed in close proximity to the infant. The fiberoptic pad 10 is basically a product that is currently on the market and is sold by the Ohmeda Division of BOC Health Care, Inc. and used for phototherapy for infants. The preferred pad is produced by a weaving optical fibers and standard threads together to form a flexible pad material that provides uniform illumination. The fiberoptic phototherapy pads are currently used by placing them in close proximity to an infant so that the light impinges on the infant to carry out the process of phototherapy.

In the present Ohmeda commercial product, a plurality of layers of woven fabric are utilized as will later be explained, but generally in accordance with the disclosure of U.S. Pat. No. 4,907,132.

In the commercial product, light radiation is supplied from a light source 12 which may be a conventional resistance bulb that is equipped with a filter to filter out unwanted wavelengths and to allow only those wavelengths that are known to be conducive to the reduction of bilirubin, that is about 440 nanometers to about 540 nanometers.

An optical fiber 14, generally in the form of a bundle of optical fibers, transmits the light radiation from light source 12 to fiberoptic phototherapy pad 10. As can be seen, that light radiation is therefore directed toward and impinges upon the infant. As used in this invention, the optical fibers may be plastic or glass.

An electric power supply 16 powers the light source 12 and, of course, also controls the intensity of the light source 12 by increasing or decreasing the power to operate light source 12. A light detecting means is provided to sense the intensity of light radiating from the fiberoptic pad 10 to impinge upon the infant. As shown, that light detecting means is a fiberoptic detector pad 18 that is preferably positioned intermediate the fiberoptic pad 10 and the infant.

As will be explained, the construction of the fiberoptic detector pad 18 is constructed as is the fiberoptic pad 10. The construction is disclosed in the aforementioned Daniel patent and consists of a woven pad wherein optic fibers and normal threads are woven together. It has been found that such construction not only makes a very effective emitter of light radiation but is a good detector of that same light radiation.

In addition, the Daniel type of construction allows the fiberoptic detector pad 18 to be relatively transparent to light radiation and therefore the fiberoptic detector pad 18 can be interposed in the best of all positions, directly between the fiberoptic pad 10 and the infant. As such, it is able to directly receive the output from the fiberoptic pad 10 as well a accurately measure, with an optical transducer, the amount of light radiation that actually impinges upon the infant.

Further, by the use of a fiberoptic pad constructed in accordance with the Daniel patent, the detection of light radiation is not at a selective spot with respect to the infant but the light is sensed over the entire area of the fiberoptic detector pad 18 which may be the same dimensions as the fiberoptic pad 10.

Accordingly, the fiberoptic detector pad 18 can be designed to sense a radiant flux and will still give a valid reading if the light is applied nonuniformly for reason of some defect in the fiberoptic pad 10 or such nonuniformity is deliberate.

The light intensity received by fiberoptic detector pad 18 is thus transmitted through optical fiber 20 to an optical transducer 22 where the optical signal indicative of light intensity is converted to an electrical signal representative thereof.

An amplifier 24 receives that electrical signal and amplifies it and feeds the amplified signal into a regulator 26 where it can be used to control electric power supply 16. Thus a user could set a desired light intensity, a signal representative of that light intensity inputted into the regulator 26 and the signal from the amplifier 24 may be compared by a comparator such that the output of the light source 12 is altered to maintain that desired light intensity, even though other factors may change such as the normal reduction is light output from a resistance bulb due to age.

Figure 2:
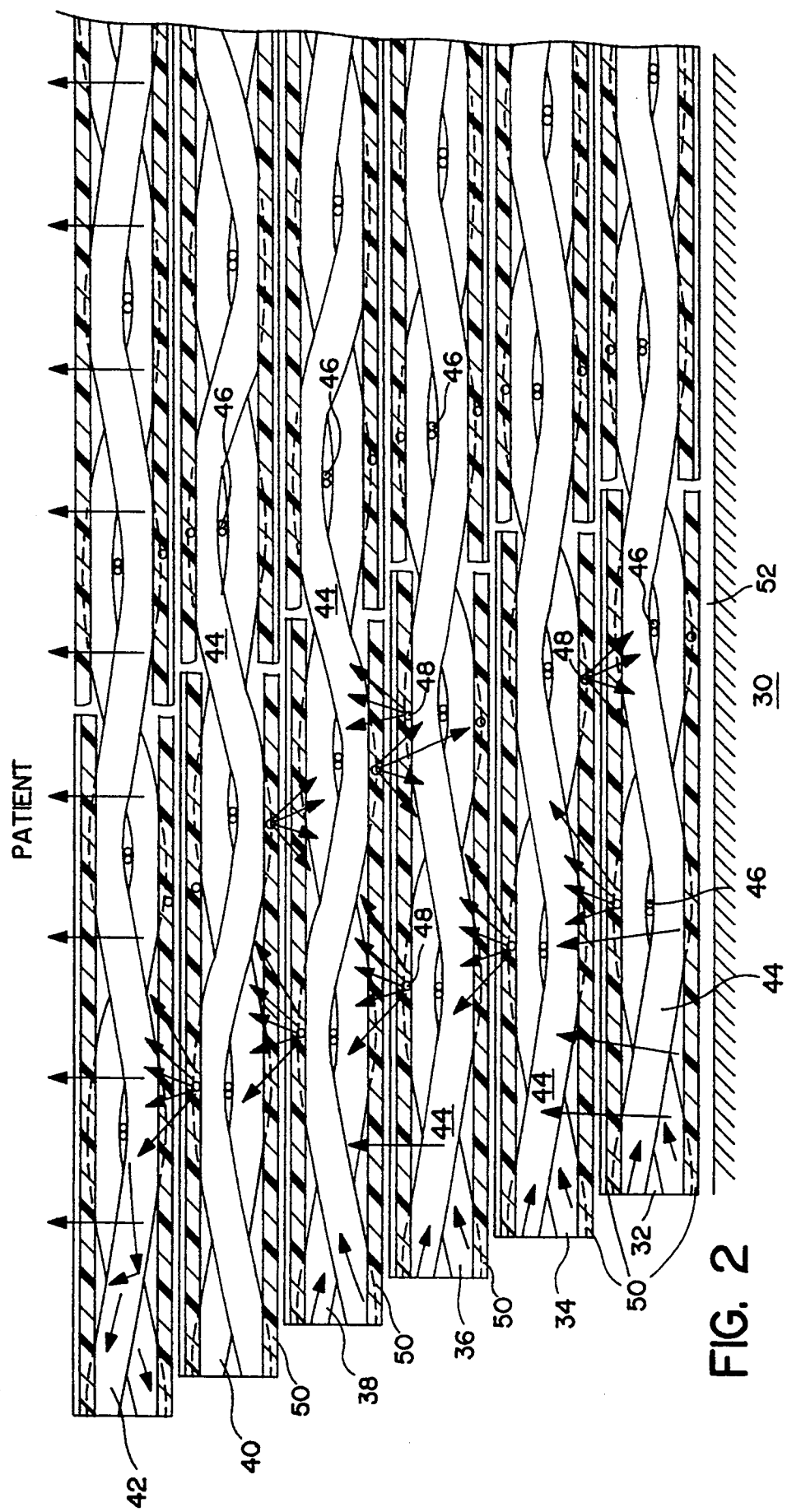
FIG. 2 is an enlarged sectional view of a light detecting means usable with the fiberoptic phototherapy system of FIG. 1.

Turning now to FIG.2, there is shown an enlarged, cross sectional view of a fiberoptic unit 30 that is usable with the phototherapy system of FIG. 1. The basic construction of the FIG. 2 embodiment is found in the commercial product, however the details of its makeup is also disclosed in U.S. Pat. No. 4,907,132, the disclosure of which is incorporated herein by reference.

In FIG. 2, the overall fiberoptic unit 30 is comprised of a plurality of layers 32, 34, 36, 38, 40 and 42 wherein the layer 42 i s facing the infant. The layers 32–40 are the normal commercial light emitting layers in the pad currently available and include optical fibers 44 woven only in the warp direction. Fill threads 46 are interwoven therewith in the weft direction. As is conventional in the weaving art, weft threads are normally carried by the shuttle of the weaving loom while the warp threads extent lengthwise of the loom, crossed by the weft threads.

In the present embodiment, however, the fill threads 46 or weft threads may preferably be made of a transparent thermoplastic such that they do not interfere with the light transmitted toward the infant by the emitting layers 32-40. Thus, optical losses are not significant.

As set forth in the aforementioned U.S. Pat. No. 4,907,1323, the illumination is caused to be emitted from the optical fibers through the bending of such fibers at a plurality of discrete locations along their length, thereby creating scattering centers 48 throughout the fiberoptic emitting layers 32-40.

One or both of the ends of the optical fibers 44 may be bundled together and formed into a plug or fiber bundle that eventually forms optical fiber 14 of FIG. 1. through which light is transmitted to the emitting layers 32-40 for phototherapy to the infant. As each of the emitting layers is formed, one or both surfaces of the layer may be coated with a coating 50 having the same or different refractive indices. The layer 32, furthermost from the infant may also have a reflective coating 52 to direct the scattered light toward the infant.

Turning now to layer 42, positioned adjacent the infant, layer 42 is a collecting or detecting layer and its optical fibers 54 receive the light radiation emitted from the emitting layers 32-40. Again, the ends of the optical fibers 54 are collected together in a bundle and which becomes the optical fiber 20 of FIG. 1 and which collects the light radiation and transmits that light back to the optical transducer 22.

As can be seen, the detecting layer 42 can, therefore, be manufactured simultaneously with the normal emitting layers 32-40 and the overall unit 30 can be supplied to the customer as one unitary product combining both emitting layers for providing phototherapy for the infant as well as a detecting layer that serves to detect the light intensity of the light radiation being directed upon the infant. Also, since the detecting layer 42 is formed of a pad having an area that may be the same surface area as the emitting layers 32-40, the emitting layer 42 receives an overall flux density of the light radiation and its sensing is not limited to specific small areas of sampling.

The FIG. 2 embodiment is readily manufacturable given the current manufacturing techniques since the overall fiberoptic pad may be produced as is the commercially available unit, the difference being that the final layer becomes the detecting layer 42 by merely collecting the optical fibers 44 into a separate bundle for connection to the optical transducer 22 instead of the light source 12.

Figure 3:
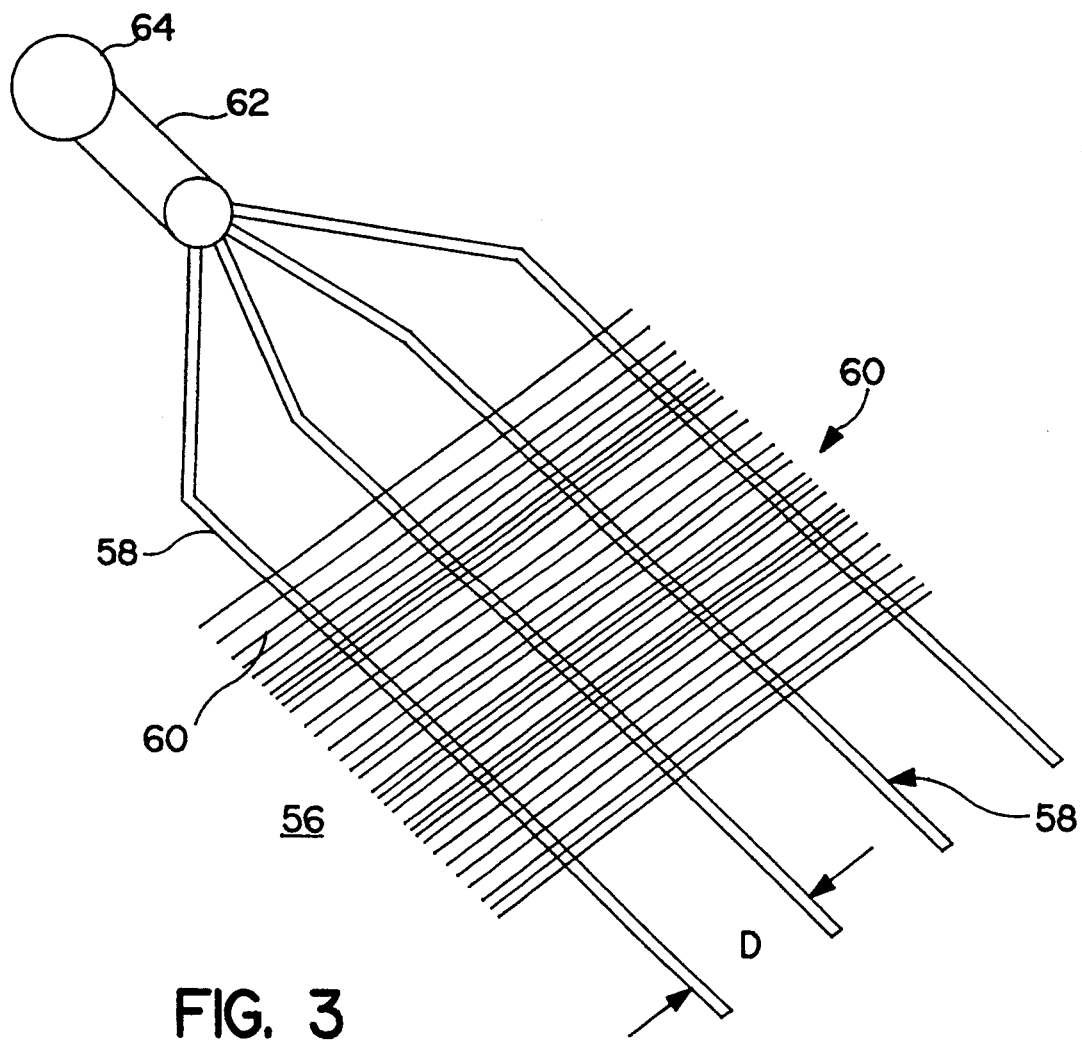
FIGS. 3-8 are schematic views of various other light detecting means usable with the phototherapy system of FIG. 1.

In FIG. 3, there is shown a schematic view of a further fiberoptic pad 56 that is usable to detect light radiation from an emitting fiberoptic pad. In the FIG. 3 embodiment, which may be manufactured as part of a multilayer pad similar to the FIG. 2 embodiment or may be separately placed between a fiberoptic phototherapy pad and an infant, a low density is achieved to allow the light radiation to reach the infant fairly unimpeded or undiminished by the positioning of the detecting fiberoptic pad 56. In this embodiment, the warp optical fibers 58 that receive the light radiation are further spaced apart and fewer fibers used than in FIG. 2. As seen, the warp optical fibers 58 are separated by a predetermined distance D which may be 3-10 times the more than the distance separating the warp fibers of an emitting layer. The weft fibers 60 may be transparent thermoplastic fibers to again cause the least reduction in the light passing between the emitting phototherapy pad and the infant.

Again, as seen in the FIG. 3, the warp optical fibers 58 are bundled together and formed into or coupled to a optical fiber 62 for transmitting the collected or detected light radiation to a optical transducer 64.

Figure 4:
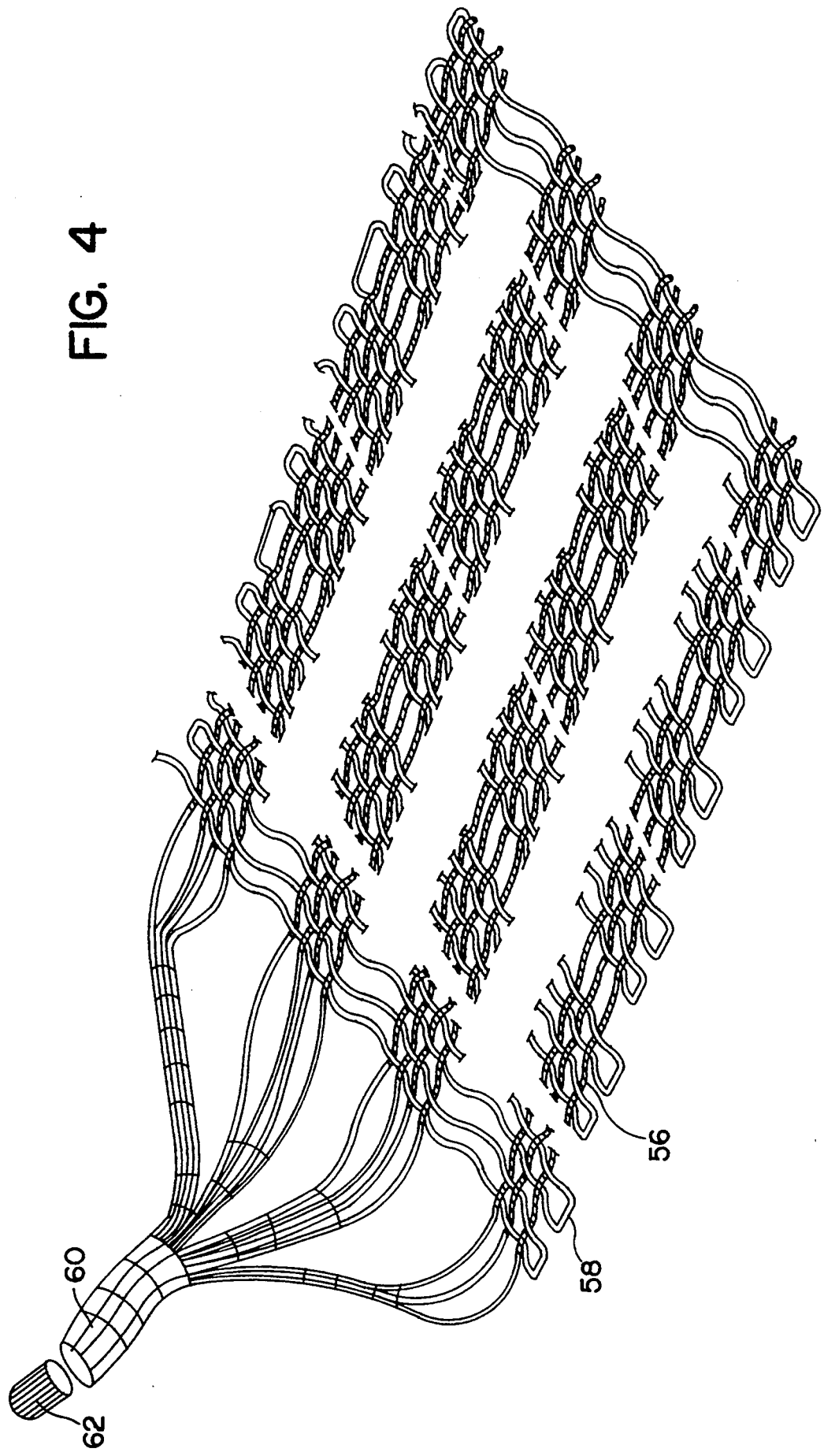
Figure 5:
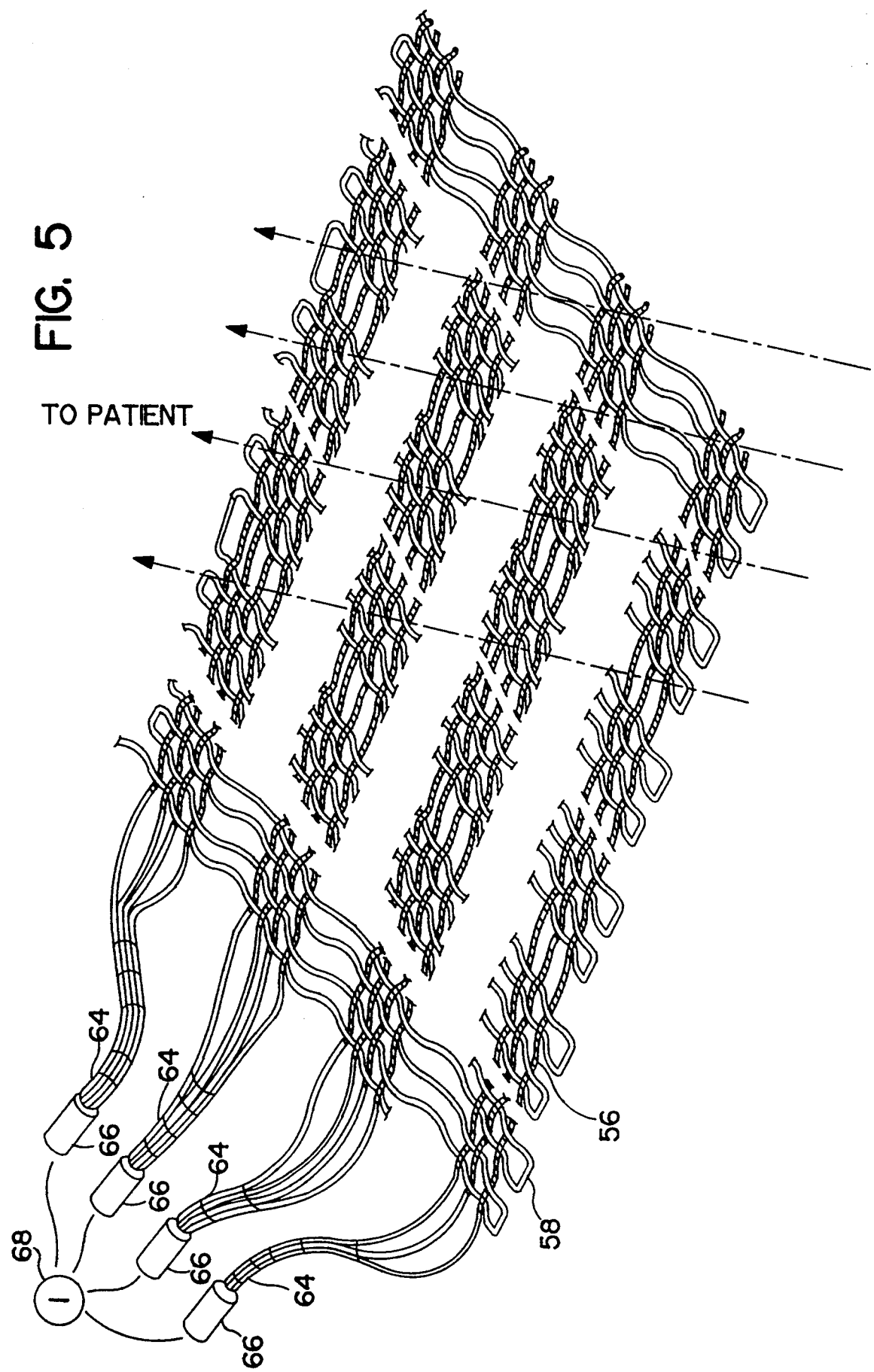

In FIGS. 4 & 5, an embodiment of the present invention is shown where strips of detecting optical fibers 56 are used to obtain a representative light density from a fiberoptic phototherapy pad (not shown). In FIG. 4, the strips of detecting optical fibers 56 are woven with weft fibers 58 and the ends are collected in a single bundle 60 for transmitting the detected light radiation to an optical transducer 62. Thus with the FIG. 4 embodiment, a value representative of the true flux density can be sensed due to the separate pad type of detectors and a cross section of the light passing to the infant can be recognized.

The FIG. 5 embodiment is constructed as the FIG. 4 embodiment except that a plurality of bundles 64 collect the light radiation and a plurality of optical transducers 66 can be used. The FIG. 4 embodiment will, of course, obtain the flux density of the light radiation over its entire area and transmit that light density to a single sensor while the FIG. 5 embodiment may be used to obtain a segregated light density analysis and can be used to determine the uniformity or variance in the intensity of the light emitted by the phototherapy pad over its surface area.

Figure 6:
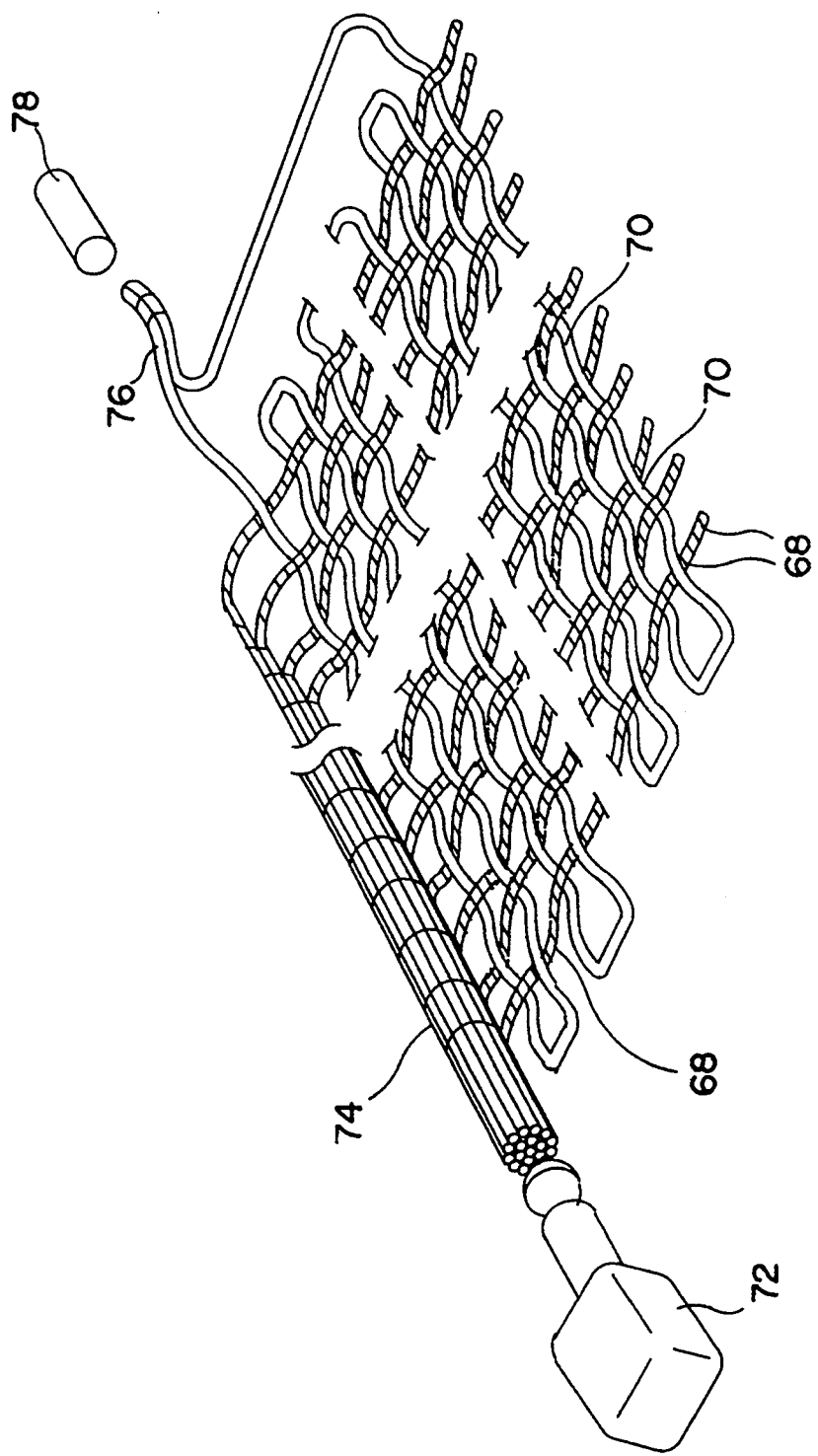

Turning now to the FIG. 6 embodiment, there is shown a schematic of yet another detecting fiberoptic pad usable with the present invention. In this embodiment, a single layer is formed by emitting warp fibers 68 woven with detecting weft fibers 70 and therefore the pad is woven with optical fibers in both the warp and the weft directions. A source of light radiation 72 supplies light through a fiberoptic bundle 74 to the light emitting warp fibers 68 while the detecting weft optical fibers 70 are formed into a fiberoptic bundle 76 and transmit the detected light radiation to a suitable optical transducer 78.

Figure 7:
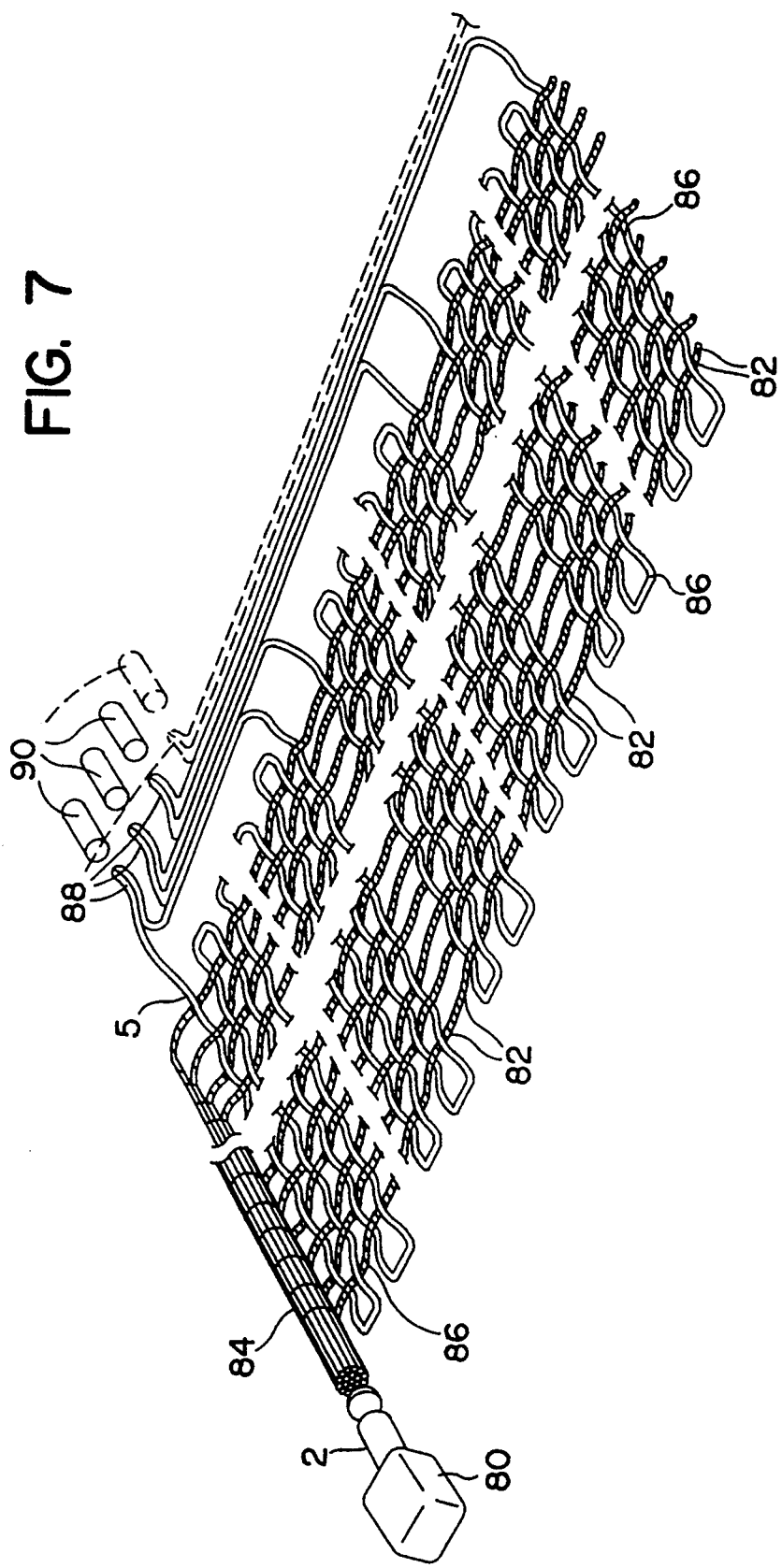
Figure 8:
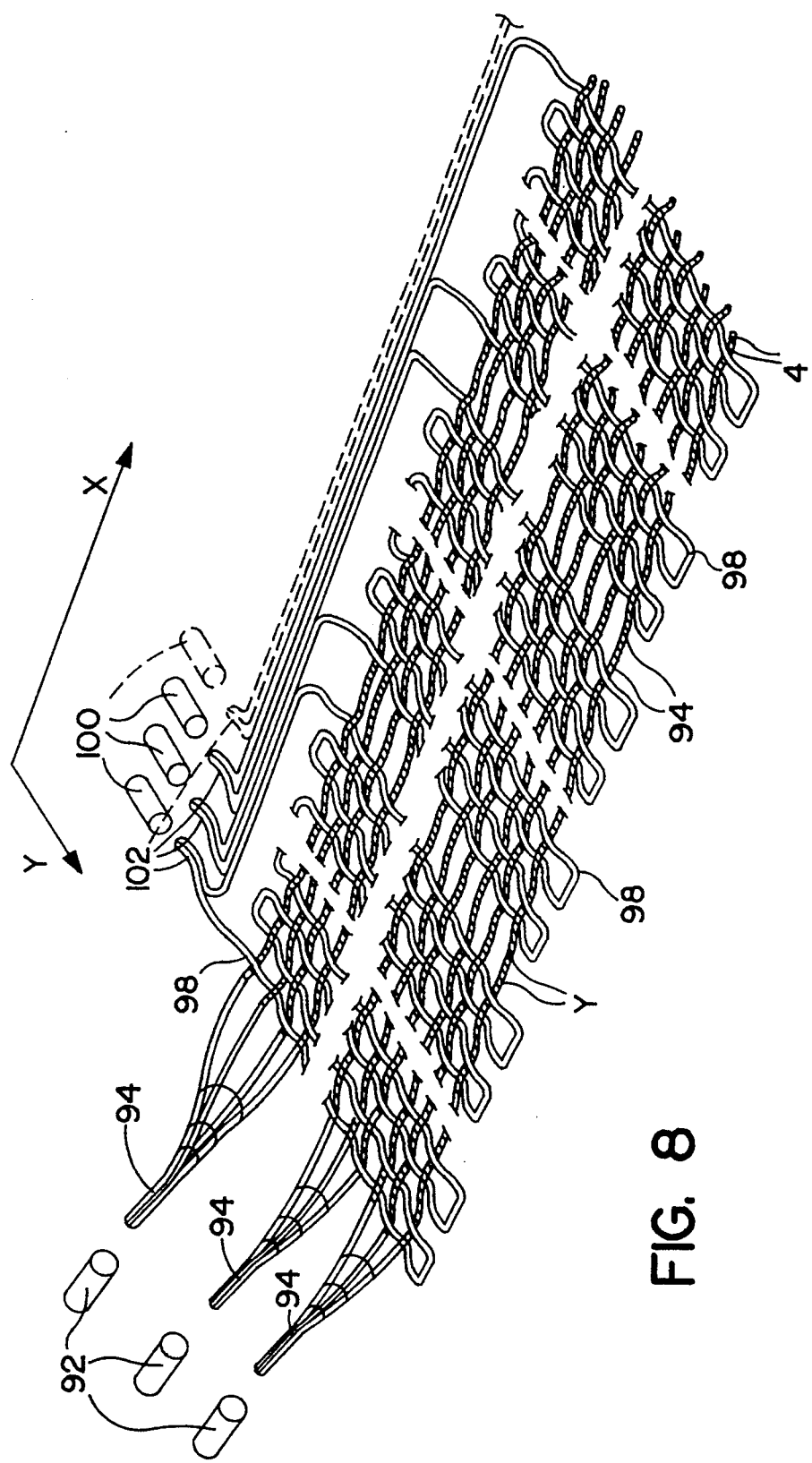

In the FIG. 7 and 8 embodiments, the same overall construction is used as the FIG, 6 embodiment, that is, a single source of light radiation 80 supplies that light to emitting warp fibers 82 through optical bundle 84. Detection of the light radiation is accomplished, however, through a plurality of discrete strips of detecting weft fibers 86 that channel the detected light radiation into individual fiberoptic bundles 88 to a plurality of optical transducers 90. In FIG. 8, a plurality of light radiation sources 92 are used to supply light radiation through discrete fiberoptic bundles 94 to stripes or arrays of light emitting warp fibers 94 so the light may be controlled across the overall fiberoptic phototherapy pad. Detection of the light density and individual control of light zones or stripes is accomplished by a plurality of arrays or stripes of detecting weft fibers 98 that detect and transmit that detected light radiation to a plurality of optical transducers 100 through groups of bundles 102.

Figure 9:
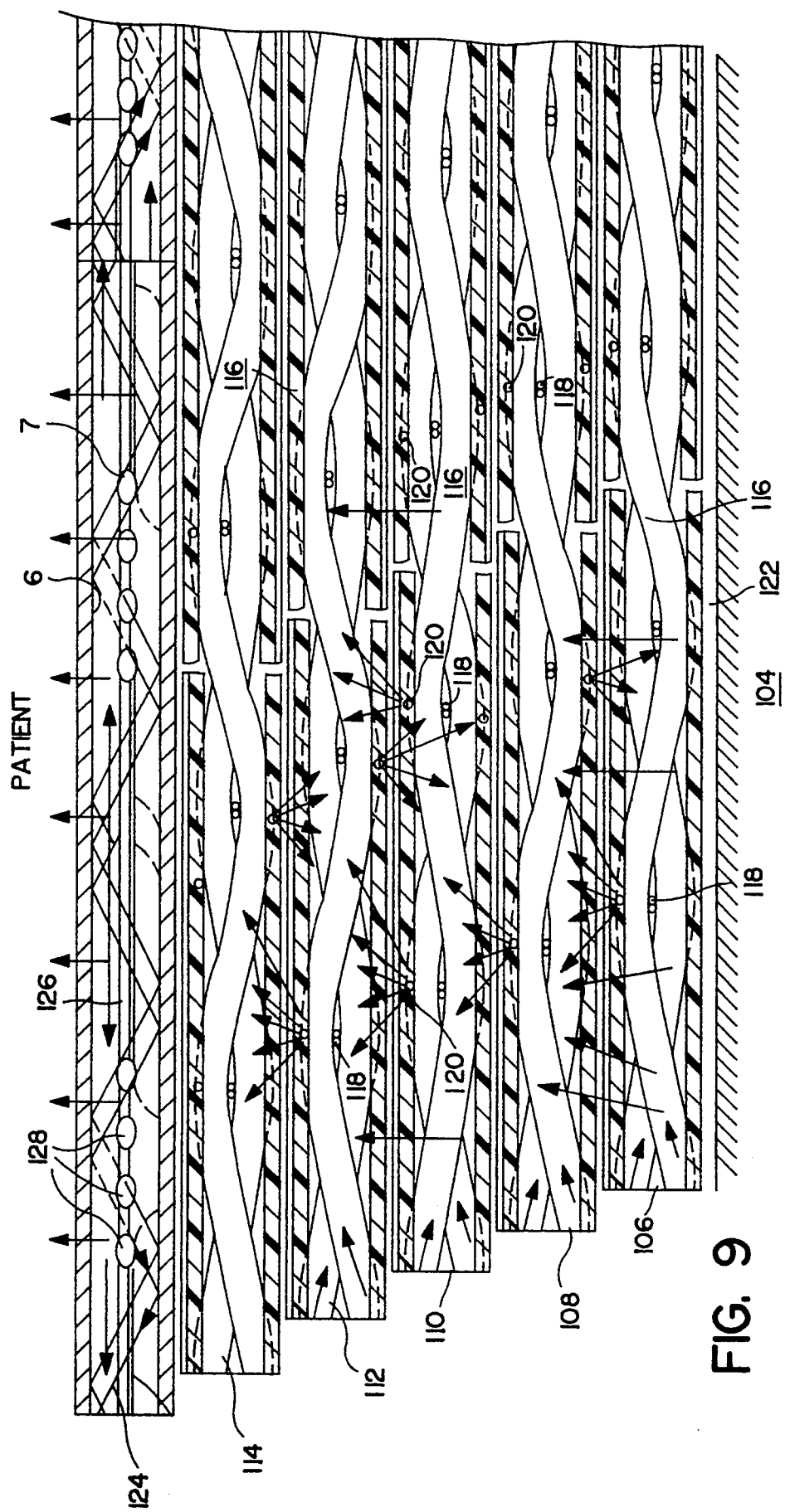
FIG. 9 is an enlarged cross-sectional view of yet another light detecting means usable with the phototherapy system of FIG. 1.

Finally, turning to FIG. 9, there is shown a multilayer phototherapy unit 104 in which emitting layers 106-114 are similar to the emitting layers of the FIG. 2 embodiment and where the emitting warp optical fibers 116 are bent sufficiently by the weft fibers 118 to create scattering centers 120 on the warp emitting fibers 116 to emit the light radiation for phototherapy. Again, a reflecting layer 122 may be formed on the surface away from the infant to assist in reflecting stray light radiation toward the infant.

In this embodiment, however, the light collecting or detecting layer 124 which again faces the infant, is constructed in accordance with U.S. Pat. No. 4,763,984 in the name of Awai et al and the disclosure of that patent is incorporated herein by reference. As one skilled in the art will recognize, the Awai et al patent refers to light scattering centers, however, those centers, as described, are non-homogeneous centers in fiber optic material and similarly, therefore, act as light collection centers if the fiber is illuminated by external scattering light. In such case, the scattered light impinging on the light collecting centers will be collected by the non-homogeneous centers and transmitted through the fiber to the end of the fiber where the light may be detected by some detecting means. In this embodiment, the detecting optical fiber 126 has a plurality of light detecting centers 128 which collect the light radiation and transmit the same to the detecting optical fiber 126 for transmission to a optical transducer (not shown). These scattering centers 128 serve as light reception centers and may be of glass, plastic or other similar materials.

While the invention has been disclosed and described with reference to a single embodiment, it will become apparent that variations and modifications may be made therein, and it is therefore intended in the following claims to cover each such variation and modification as falls within the true spirit and scope of the invention.

We claim:

1. A system for delivering light radiation to the skin of an infant for phototherapy, said system comprising:
   (a) a light source for producing light of a known wavelength suitable for phototherapy,
   (b) a fiberoptic light emitting pad comprising a plurality of emitting optical fibers adapted to be positioned in close proximity to an infant,
   (c) means to transmit the light radiation from said light source to said plurality of emitting optical fibers to cause said fiberoptic light emitting pad to emit light radiation transmitted from said light source to impinge upon the skin of the infant,
   (d) a light detector for receiving and quantifying the amount of light received,
   (e) a light collecting pad interposed between said fiberoptic light emitting pad and the infant, said light collecting pad comprising a plurality of optical fibers and collecting light emitted from said light emitting pad, and
   (f) means to transmit the light radiation collected by said light collecting pad to said detector to detect the light radiation emitted by said light emitting pad.

2. A system as defined in claim 1 wherein said light collecting pad comprises a pad having a plurality of optical fibers interwoven with fill fibers.

3. A system as defined in claim 2 wherein said fill fibers are light transparent fibers of a thermoplastic material.

4. A system as defined in claim 1 wherein said light emitting pad and said light collecting pad are combined into a unitary construction.

5. A system as defined in claim 4 wherein said light emitting pad comprises a plurality of layers of interwoven light emitting optical fibers.

6. A system as defined in claim 5 wherein said light collecting pad comprises a layer of light collecting optical fibers overlying said plurality of layers of light emitting optical fibers and is located in closest proximity to the infant.

7. A system as defined in claim 1 wherein said light collecting pad comprises a plurality of weft fibers comprised of a transparent thermoplastic material spaced apart a predetermined distance and a plurality of warp fibers comprised of light detecting optical fibers spaced apart a distance of about 3-10 times the distance between said emitting optical fibers.

8. A system as defined in claim 1 wherein said light collecting pad comprises a plurality of discrete sections of light detecting optical fibers interwoven with fill fibers, said discrete sections having at least one set of ends interwoven together.

9. A system as defined in claim 1 wherein said light collecting pad comprises a plurality of discrete sections of light detecting optical fibers interwoven with fill fibers, each of said discrete sections having its ends interwoven together independent of the ends of said other discrete sections.

10. A system for delivering light radiation to the skin of an infant for phototherapy, said system comprising:
    (a) a light source for producing light of a known wavelength suitable for phototherapy,
    (b) a fiberoptic light emitting and collecting pad comprising a plurality of emitting and collecting optical fibers adapted to be positioned in close proximity to an infant,
    (c) means to transmit the light radiation from said light source to one or more of said plurality of emitting optical fibers to cause said fiberoptic light emitting pad to emit light radiation transmitted from said light source to impinge upon the skin of the infant,
    (d) a light detector for receiving and quantifying the amount of light received, and
    (e) means to transmit the light radiation collected by one or more of said light collecting optical fibers to said detector to detect the light radiation emitted by said light emitting optical fibers.

11. A system as defined In claim 10 wherein said light emitting optical fibers are woven in the warp direction and said light detecting optical fibers are woven in the weft direction.

12. A system as defined in claim 10 wherein said light emitting optical fibers are woven in the weft direction and said light detecting optical fibers are woven in the warp direction.

13. A system as defined in claim 10 wherein said light emitting optical fibers are formed in discrete groups of fibers, each of said groups having its ends woven together into separate bundles of light emitting optical fibers.

14. A system as defined in claim 10 wherein said light detecting optical fibers are formed in discrete groups of fibers, each of said groups having its ends woven together into separate bundles of light detecting optical fibers.

15. A system as defined in claim 1 wherein said light collecting pad comprises a plurality of light collecting optical fibers having light absorption centers formed along said light collecting optical fibers, said light absorption centers located at predetermined spacing along said light collecting optical fibers.

16. A system for controlling the amount of light applied to the skin of an infant for phototherapy, said system comprising;
   (a) a light source for generating light,
   (b) a fiberoptic pad adapted to be positioned in close proximity to the infant, said fiberoptic pad receiving light from said light source and transmitting that light to impinge upon the infant,
   (c) a light collecting means interposed between said fiberoptic pad and the infant, said light detecting means collecting the intensity of light transmitted from said fiberoptic pad to the infant, and
   (d) means to control the intensity of the light transmitted from from said fiberoptic pad to the infant dependent on the light intensity detected by said light collecting means.

17. A light collecting means for use with a light detector for detecting the amount of light impinging upon an infant for phototherapy, said light detecting means comprising a light collecting fiberoptic pad adapted to be positioned in close proximity to the infant to receive light radiation impinging upon the infant, said light collecting fiberoptic pad comprising a fiberoptic light pad having a plurality of light collecting optical fibers interwoven together, said optical fibers being processed so as to receive light along the length thereof and to transmit that light along the individual optical fibers to external ends of said optical fibers, and a connector means at said ends of said optical fibers for transmitting the light collected by the light detecting pad to the light detector.

18. A light detecting means as defined in claim 17 wherein said optical fibers are interwoven with fill fibers.

19. A light detecting means as defined in claim 18 wherein said fill fibers are light transparent fibers of a thermoplastic material.

20. A light detecting and light emitting interwoven fiberoptic pad for use with a light source and a light detector to provide light phototherapy to an infant, said fiberoptic pad adapted to be located in close proximity to the infant, said fiberoptic pad comprising light emitting optical fibers and light collecting optical fibers interwoven together, said light emitting optical fibers having a connector means adapted to receive light radiation from the light source and to emit that received radiation toward the infant, and said light collecting optical fibers located adjacent the infant to collect representative light emitted by said light emitting optical fibers impinging upon the infant and having a connector means to collect such detected light for transmission therefrom to the light detector.

21. An interwoven fiberoptic pad as defined in claim 20 wherein said emitting optical fibers are woven at about a 90 degree angle to said collecting optical fibers.

22. An interwoven fiberoptic pad as defined in claim 21 wherein said emitting optical fibers are woven in the warp direction and said collecting optical fibers are woven in the weft direction.

23. An interwoven fiberoptic pad as defined in claim 21 wherein said emitting optical fibers are woven in the weft direction and said collecting optical fibers are woven in the warp direction.

24. An interwoven fiberoptic pad as defined in claim 20 wherein said emitting optical fibers comprise a plurality of discrete sections and said connector means comprises a plurality of connectors, each of said plurality of connectors being affixed to one of said discrete sections.

25. A multilayer fiberoptic pad for administering light radiation to an infant for phototherapy and adapted to be located in close proximity to the infant, said fiberoptic pad comprising a plurality of layers of light emitting optical fibers interwoven together and adapted to receive light from a light source having a predetermined wavelength and to emit light toward the infant, at least one layer of light collecting optical fibers interwoven together and located intermediate said plurality of layers of light emitting optical fibers and the infant, said at least one layer of collecting optical fibers adapted to collect light radiation emitted by said emitting optical fibers and to transmit the collected light to a light detector to detect the intensity of light radiation impinging upon the infant.

26. A fiberoptic pad as defined In claim 25 wherein said at least one layer of interwoven collecting optical fibers comprises collecting optical fibers interwoven with fill threads composed of a transparent thermoplastic material.

27. A system for providing light radiation to an infant for phototherapy, said system comprising:
   (a) a light emitting fiberoptic pad for conducting light for impingement upon an infant for phototherapy, said pad comprising a plurality of optical fibers interwoven together to form said pad,
   (b) a light source means adapted to transmit light into some of said optical fibers within said fiberoptic pad
   (c) light detector means adapted to receive light impinging upon others of said optical fibers within said fiberoptic pad, and
   (d) control means adapted to control the intensity of light emitted from said light emitting pad based upon the light received by said light receiving means.

28. A system as defined in claim 27 wherein said control means includes a memory and controls the light emitted from said light emitting fibers in accordance with a preset light dosage stored in said memory.

* * * * *